United States Patent
Samchukov et al.

[11] Patent Number: 5,980,252
[45] Date of Patent: Nov. 9, 1999

[54] DEVICE AND METHOD FOR ENHANCING THE SHAPE, MASS, AND STRENGTH OF ALVEOLAR AND INTRAMEMBRANOUS BONE

[76] Inventors: Mikhail L. Samchukov, 726 Cheshire Dr., Coppell, Tex. 75019; Rohit C. L. Sachdeva, 2605 Courtside Ln., Plano, Tex. 75093; J. David Ross, 1310 Red Oak Creek Rd., Ovilla, Tex. 75154

[21] Appl. No.: 08/436,747

[22] Filed: May 8, 1995

[51] Int. Cl.$^6$ ..................................................... A61C 5/00
[52] U.S. Cl. .............................. 433/215; 433/172; 623/16
[58] Field of Search ................................... 433/215, 229, 433/172, 173, 174, 175; 606/60, 76, 86, 53, 54, 105, 57, 63, 68; 623/17, 18

[56] References Cited

U.S. PATENT DOCUMENTS

| | | | |
|---|---|---|---|
| 4,502,160 | 3/1985 | Moore et al. | 623/18 |
| 4,682,951 | 7/1987 | Linkow | 433/173 |
| 4,932,975 | 6/1990 | Main et al. | 623/17 |
| 4,961,707 | 10/1990 | Magnusson et al. | 433/215 |
| 5,147,402 | 9/1992 | Bohler et al. | 606/60 |
| 5,171,278 | 12/1992 | Pisharodi | 623/17 |
| 5,358,524 | 10/1994 | Richelsoph | 623/18 |
| 5,413,602 | 5/1995 | Metz-Stavenhagen | 623/17 |
| 5,455,041 | 10/1995 | Genco et al. | 433/215 |
| 5,507,746 | 4/1996 | Lin | 606/60 |
| 5,511,565 | 4/1996 | Syers | 433/229 |

FOREIGN PATENT DOCUMENTS

| | | |
|---|---|---|
| 167008 | 1/1965 | Russian Federation. |
| 223255 | 11/1968 | Russian Federation. |
| 921546 | 4/1982 | Russian Federation. |

OTHER PUBLICATIONS

"Composite Graft for Mandibular Alveolar Ridge Augmentation: A Preliminary Report", Kraut, *J Oral Maxillofac Surg*, 43:856–859, 1985.

"Treatment of the Mandibular Compromized Ridge: A Literature Review", Jennings, *J of Prosthetic Dentistry*, 61: 575–579, May, 1989.

"Preventive Goals in Oral Implantology", Kalk, et al, *International Dental Journal*, 43:483–491, 1993.

"Surgical and Prosthodontic Residual Ridge Reconstruction with Hydroxyapatite", Zeltser, et al, *J of Prosthetic Dentistry*, 62:441–448, Oct. 1989.

*Primary Examiner*—John J. Wilson
*Attorney, Agent, or Firm*—Wood, Herron & Evans, L.L.P,

[57] ABSTRACT

A device and method is presented for enhancing the shape, mass, and strength of alveolar and intramembranous bone, primarily in areas of bony deficit. In one embodiment, the device is made up of a hollow body which forms a housing to contain a drive train and provide a surface for attaching mounting elements. A worm gear activating element which meshes with a threaded lead screw acts as the drive train. A carrier is coupled by threads to the lead screw. As the worm gear is turned, the lead screw rotates and causes the carrier to move along the axis of rotation of the lead screw. In this embodiment, the soft tissue in a region of tooth loss is reflected to expose the atrophic bone site. A piece of bone harvested from the exposed area or other bone attractant material is attached to the carrier. The soft tissue is adapted over the carrier and sutured, and the assembly is attached to available dental structures. After initiation of biological bridging between the harvested bone and the host bone, the drive train is activated to move the carrier. Newly formed bone grows in the path of motion of the carrier between the harvested bone and the underlying bone.

20 Claims, 10 Drawing Sheets

DEVICE AND METHOD FOR ENHANCING THE SHAPE, MASS, AND STRENGTH OF ALVEOLAR AND INTRAMEMBRANOUS BONE

This invention relates to a device and method for restoring the mass and shape of bones of the dentoalveolar complex and its related anatomy such as the palatal shelves. More particularly, this device provides a frame which attaches to the dentoalveolar anatomy and adjacent structures, and a screw-operated movement fixture which carries a specimen of material that encourages the development and the distribution of new bone tissue, and which, more particularly, provides the means to restore or augment areas of bony deficit with new homologous bone.

BACKGROUND OF THE INVENTION

The teeth are anchored in alveolar bone which is a highly vascularized bony tissue specialized in supporting the teeth. The alveolar bone in turn is supported by intramembranous bone. Such bone is only found in the region of the skull. Bone is covered by a rich fibrous layer of tissue called the periosteum which acts as a reservoir for bone producing cells.

Alveolar bone forms a ridge or process which surrounds and supports the teeth. When a tooth is lost due to injury or disease, the section of alveolar bone which supported the tooth is rapidly resorbed by the body. Much of the original mass and strength of the bone is lost through this natural remodeling process. Atrophy or loss of alveolar bone may also occur as the result of trauma to the bone, infection, radiation, congenital abnormalities or degenerative bone diseases. The severity of thinning or atrophy relates to the number of teeth lost and the time elapsed since the occurrence of the loss. The alveolar bone eventually becomes so thin and fragile that it can not reliably support dental prostheses or implants. A loss of chewing efficiency results which, in turn, gives rise to other problems such as uneven tooth wear, tooth migration, fractures, infection and facial deformity.

The general approach to the treatment of tooth loss is to attempt to restore function by fitting a prosthesis, dental implant, or through orthodontic intervention. These efforts become more difficult and less successful when bone loss has occurred. Unfortunately, when they fail, additional bone is lost, remodeling continues, and the potential for future correction is diminished.

Implants often fail because there is not enough bone mass available to support them. In younger patients, implants do not maintain the same height as neighboring teeth, which erupt as part of the natural growth and development process of the craniofacial complex. Over time, these implants submerge with respect to the adjacent teeth, reducing chewing efficiency and forming a trap for food debris and bacteria. This condition promotes infection of the bone surrounding the implant and leads to bone loosening and eventual failure of the implant. In the upper jaw, tooth loss can initiate an undesirable remodeling of the bony walls of the sinuses. As this bone thins out, and the sinus expands, it becomes difficult to fit a prosthesis or implant.

Edentulous patients suffer ongoing bone loss as the alveolar ridges are resorped. This leads to knife edge ridges which are ineffective in supporting prostheses such as dentures.

Moving teeth through atrophic alveolar ridges during orthodontic treatment leads to a number of problems. One in particular is the occurrence of root exposure as the teeth are moved through the atrophic bone. Periodontal disease and tooth loss can follow.

To overcome this, grafts of bone or biocompatible materials such as hydroxylapatite are used to increase the bone mass in areas of bony atrophy. Unfortunately, such procedures have high morbidity and a relatively low success rate. The results are unpredictable at best. Another problem is that after implantation, bone grafts must be shielded from loading until the graft takes. During this time, the graft undergoes remodeling, making it difficult to predict the final size and shape of the augmented alveolar ridge. The bone graft may also be rejected with subsequent failure of ridge augmentation.

Replacement of bone with hydroxylapatite may help regain some of the lost support in the area, but teeth cannot be moved through this bone substitute. Implants that are anchored in hydroxylapatite have a high failure rate due to mechanical breakdown at the hydroxylapatite-implant junction. Hydroxylapatite is also difficult to shape and is never as strong as natural bone. Some replacement of hydroxylapatite by new bone tissue does occur in the body but this material is never completely replaced by new bone.

Bone grafting and the use of hydroxylapatite is a traumatic and expensive procedure which requires a significant amount of time for healing to take place.

Defects also occur in the intramembranous bone. For instance, these may be caused during the extraction of teeth leading to oro-nasal fistulae. These are openings between the mouth and the sinuses. They are generally closed by placing grafts of gum tissue over the deficit. For large defects, the success of such grafts is limited. The treatment of such defects is best served by restoring the structure and shape of the area of lost bone.

Also, developmental defects occur in intramembranous bone, such as is seen in the clefts of the palate. In these anomalies, patients are born with defects of intramembranous bone in the roof of the mouth. Filling of these defects requires multiple surgeries over the individual's lifetime with bone and soft tissue grafts. Usually the results accomplished through such procedures only partially restore the shape, mass, and strength of the bone in the roof of the mouth.

Dental endosseous implants are subject to both axial and lateral stresses during mastication. An approach to stabilizing against lateral stresses uses implants which have the tooth embedded parts widened by either using the shape memory effect or the use of a wedge bolt post implantation. However, these approaches are not reliable and do not provide adequate lateral stabilization. Such implants also can not be used in areas were bone mass and strength are lacking.

The object of this invention is to provide a device and method for enhancing the shape and increasing the mechanical strength of alveolar and intramembranous bone. It functions by promoting the growth of new alveolar and intramembranous bone in a rapid and predictable manner where loss of this bone has occurred.

SUMMARY OF THE INVENTION

In accordance with the present invention, a method of enhancing the shape, mass, and strength of alveolar and intramembranous bone comprises cutting a piece of bone or providing another bone attractant material to an area of bony deficit. After a period of time, biological bridging occurs, and new bone begins to form. The bone attractant material is moved away from the defect area in a controlled manner and new bone is formed in the direction of movement. A device of the present invention to accomplish this method comprises a hollow body which forms a housing to contain the drive train and provide a surface for attaching mounting elements; a worm gear activating element with recessed hex sockets at each end; a threaded lead screw which couples to the worm gear activating element; and a carrier which is coupled to the lead screw external to the body of the apparatus.

The lead screw is constructed of any bio-compatible material, for example metals such as titanium and its alloys; nickel titanium alloys; zirconia and its alloys; iron and its alloys; and chrome cobalt alloys. The lead screw may be constructed of ceramic materials, such as aluminum oxide, zirconium oxide, titanium oxide, and hydroxylapatite. Fiber reinforced plastics and composites can be used in the construction of the lead screw as well. Bio-absorbable materials, such as poly-L-lactate and polyglycolic acids can be used for the lead screw. In addition, these materials may be used in combination with each other. The lead screw may also be coated with a shielding material to inhibit the growth of soft tissue into the bone growth area. The materials listed are exemplary and in no way limit the materials which can be used in the present invention. The lead screw can be solid or hollow to allow infusion of materials, such as bone morphogenic proteins or antibiotics, directly into the developing bone regenerate. The hollow lead screw can also allow for entry of fiber optic devices which are used to visually monitor the regeneration site. Furthermore, electromagnetic or electromechanical probes can be inserted into the area of new regenerate to monitor or stimulate new bone formation. Whether solid or hollow, the lead screw has a thread pitch designed to induce a certain desired translational displacement of the carrier for each rotation of the screw. The lead screw passes through a non-threaded hole in the housing and is mechanically retained to prevent motion in any direction except rotation about the center axis of the screw. One end of the lead screw contains a toothed head which couples with the worm screw and causes the lead screw to rotate when the worm screw is turned. The other end of the lead screw passes through a like-threaded hole in the center of the carrier plate. The rectangular shape of the carrier plate and lateral pressure from adjoining tissues prevent the carrier plate from rotating when the lead screw turns. Therefore, it is forced to translate. Also, in situations where rapid closure across large areas of bone are required, the lead screw can be constructed to activate two opposing carriers toward each other. The threaded portion of the lead screw is divided into two regions. One region has, for example, a larger diameter with a right-handed thread pitch. The other has, for example, a smaller diameter and a left-handed thread pitch. One carrier is placed on each portion of the lead screw. As the lead screw is rotated, the carriers translate from the ends of the lead screw toward the center.

In situations where it is desirable to utilize rotation of the carrier instead of translation to stimulate and distribute regenerate bone, the carrier is locked to the lead screw so that it rotates with the lead screw instead of translating along the lead screw. The carrier and any attached bone attractant material is then slowly rotated within or swept through the area of bony deficit to facilitate augmentation.

Rotating, vertically oriented carriers can also be used for translating pieces of bone attractant material away from each other thereby generating new bone.

The carrier is constructed of any bio-compatible material, for example metals such as titanium and its alloys; nickel titanium alloys; zirconia and its alloys; iron and its alloys; and chrome cobalt alloys. The carrier may be constructed of ceramic materials, such as aluminum oxide, zirconium oxide, titanium oxide, and hydroxylapatite. Fiber reinforced plastics and composites can be used in the construction of the carrier as well. Bio-absorbable materials, such as poly-L-lactate and polyglycolic acids can be used for the carrier. In addition, these materials may be used in combination with each other. The lead screw may also be coated with a shielding material to inhibit the growth of soft tissue into the bone growth area. The materials listed are exemplary and in no way limit the materials which can be used in the present invention. The carrier and the lead screw may be enveloped by shielding materials such as Goretex™ to prevent the down growth of any gum tissue from the oral side of device and therefore the development of fibrous tissue in and around the regenerate area. In some embodiments, the carrier used to support and transport a freshly harvested fragment of bone which has been attached to it. Alternatively, the lead screw may be directly attached to the bone fragment through a like-threaded hole and translated without a carrier. This bone acts as an attractant or lure to bone cells. This bone may be acutely repositioned to increase the contact area of the bone forming surfaces. The bone fragment or fragments held in the carrier can either be translated or rotated in the desired plane of space. The motion of the fragment or fragments of bone being key to the generation of new bone, its distribution and shape.

Materials other than fresh bone can also be attached to the carrier to serve as an "artificial lure". Inserting together with or instead of host bone, osteoconductive or osteoinductive materials such as bone from different areas of the body, or donor bone. Furthermore, natural or synthetic bone cements, fibrin mesh, collagen sponge, clotted blood, biocompatible metals with and without bio-active surface treatments, antibiotic impregnated materials, porous materials, corals, demineralized bone matrix materials, screen or mesh materials, bioabsorbable materials, fiber reinforced plastics and cements, ceramics, and any substrate which will attract bone cells and can be moved at an appropriate controlled rate to stimulate the growth of new bone tissue such that after this material has been moved a certain prescribed distance, the defect will be completely filled with viable new bone. In addition, the surface of the carrier can be treated to form a textured surface or porous matrix which is attractive to bone cells. Or it can be pre-treated with chemicals such as bone morphogenic protein and antibiotics. Alternatively, live cultured cells with the capacity of producing bone or bone-forming cells can be attached to the carrier alone or in conjunction with osteoconductive or osteoinductive materials. The carrier can also be constructed of bio-absorbable material that could be left in place at the end of the reconstructive period to be gradually replaced by new bone.

When the carrier is used to support and transport a segment of natural bone or other attractant material, the shape of the material acts as a template which influences the shape of the column of new bone. In some instances, the carrier can be placed between the periosteum and the adjacent bone in an area of bone loss and used to gradually pull the periosteum away from the bone without the attachment of any other material. The gradual translation of the periosteum stimulates bone growth between the adjoining surfaces of the periosteum and the bone.

The carrier is normally attached to the outer surface of the fragment so that the inner surface of the fragment can be placed in intimate contact with the resected bone prior to the beginning of translation. Then, after a certain latency period, translation begins and the fragment is slowly pulled away in an incremental or continuously gradually moving fashion. At the end of translation, the carrier is located on top of the new bone so it can be easily separated and removed. However, in some cases, it is desirable to leave the carrier submerged and enmeshed in the new bone to act as an anchor for a dental implant. When this is the case, the bone segment is secured to the outer face of the carrier and the carrier is constructed of a highly perforated or mesh material. This allows contact between the bones during translation and provides channels for bone ingrowth. At the end of translation, the carrier is left embedded between the bone fragment and the new bone. The lead screw is replace by a threaded implant which also embeds in the new bone as it mineralizes. This rod and plate arrangement then provides a solid foundation for the attachment of a dental prosthesis.

In situations where the dental prosthetic implant is submerged and requires elevation, a separate segment of bone which contains the implant such that it remains partially or completely embedded in the segment of bone may be moved to the desired position where it will be statically held until surrounded by new bone. In this procedure, the dental prosthesis is removed and a double lead screw embodiment of the apparatus is applied. The implant is attached to the center of the carrier plate with a screw. The bone surrounding the implant is then cut and gradually moved along with the implant to the desired position. Two lead screws are required so that the carrier can be positioned over the center of the implant and the necessary clearance is provided so that the implant and bone fragment do not collide with the lead screws.

The mounting plate or frame of the device can be mounted to dental structures on either side of the gap where the bone loss has occurred by either cementing, bonding and or mechanical fixation. Dental structures are defined as natural dental structures, surrounding anatomy, or implanted structures. Post or screws of bio-compatible material may also be implanted in sites adjacent to the bone defect to carry the mounting plate. The mounting plate may be attached to these. In the totally edentulous patient, the mounting plate can also be directly attached to the bone.

In some cases, where a wide section of alveolar ridge must be augmented or where it is desirable to have some control over the angle of the new bone, a double lead screw device can be used. This also has the advantage of providing additional stability. Where independent control of each lead screw is not required, they can be geared together for convenience. Only one screw then, must be turned to activate both lead screws. A double lead screw device is well suited to elevating endosseous implants. The lead screws are located near the ends of the device instead of in the center so they do not impinge on the implant or supporting bone. A hole in the center of the carrier plate allows it to be attached to the implant with a screw. In cases where space is at a premium, it may be desirable to use an embodiment of the device where the transport screw or screws are turned directly. Thus, eliminating the need for a gear train and permitting the device to be extremely compact. Another preferred embodiment would include a plate which would be placed in the bottom of the resected area beneath the bone fragment and carrier plate. It would not translate but remain in position where it would be overgrown by the new bone. It would have a porous or mesh composition that would encourage bone ingrowth and provide additional strength to the regenerate bone much as reinforcing materials strengthen concrete. After consolidation of the new bone, the plate would provide an ideal anchor to be used with or instead of endosseous dental implants. It would also be possible to use a plate formed of accordion like folds of a mesh material. The bottom fold would be attached to the bone in the bottom of the resected area and the top fold would be connected to the carrier or the bone fragment. The material would then unfold as the carrier is translated and form a reinforcing structure throughout the area of new bone.

DESCRIPTION OF THE PREFERRED EMBODIMENTS

Figure 1A:
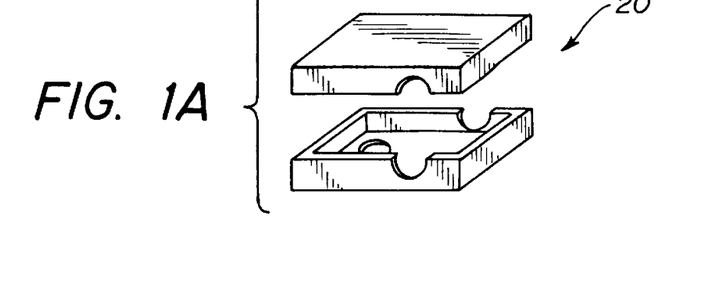
FIG. 1a is a pictorial view of the two halves of the body of the present invention.
Figure 1B:
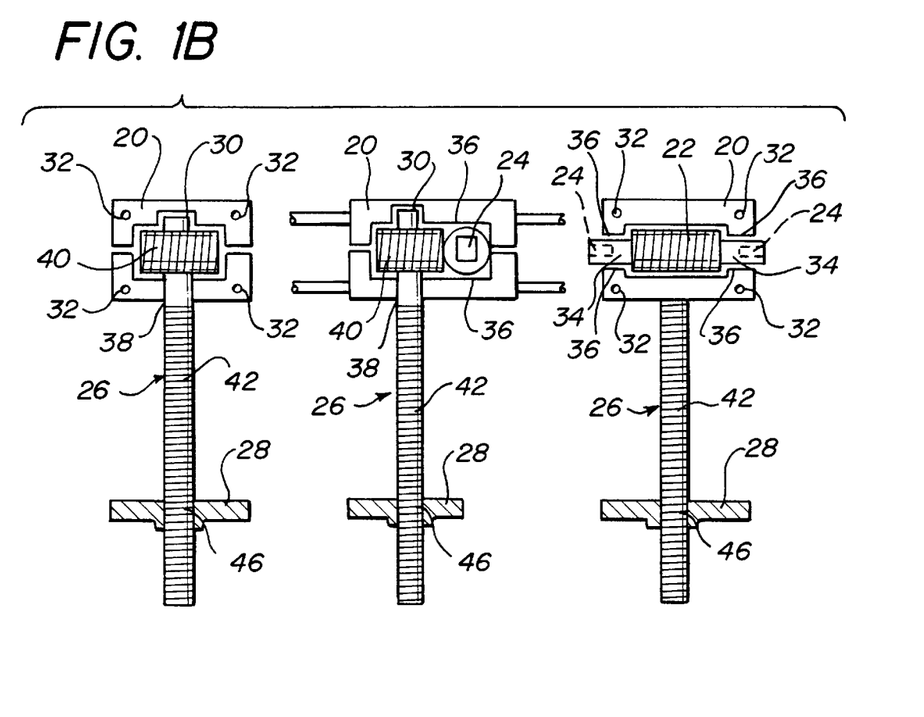
FIG. 1b provides left side, front, and right side views of one embodiment of the present invention.

Referring to FIGS. 1a and 1a, one embodiment of a bone transport device is depicted which is formed of four major components: a hollow body 20 in two halves which forms a housing for the drive train and a mounting surface for attaching the device; a worm gear 22 with recessed hex sockets 24 at each end; a lead screw 26 which couples to the worm gear 22; and a carrier 28 which is coupled to the lead screw 26.

In general, a fragment of bone is harvested from the area of bone which is to be augmented and is attached to the carrier 28 of the device. The device is attached to the dentition and adjusted so that the fragment is placed in contact with the host bone at the bottom of the area of deficit. Various methods of attachment, such as gluing, bonding, cementing, wiring and screwing can be used to secure the device in place. Then, gradually over a period of time, the carrier 28 and the bone fragment are moved away from the initial point of contact by turning the lead screw actuator. The presence and motion of the bone fragment and carrier 28 in the area of bony deficit stimulates the natural bone healing process. As a result, new bone tissue forms in the gap between the bone fragment and the host bone. New bone continues to grow and fill the gap as the translation proceeds. When sufficient new bone has formed, translation is halted and the new bone is left to mature and consolidate.

The body 20 of the device is formed of two halves which form a cavity when the two halves are joined together. This cavity is designed to accommodate and retain the worm gear 22 and the head 30 of the lead screw 26. Mounting holes 32 in each half are used to secure the device to the dentition.

The worm gear 22 provides a convenient means for accessing and rotating the lead screw 26. While this is the preferred means of activation, it is intended that other mechanisms for rotating the lead screw 26, such as direct access and rotation of the lead screw 26 when space is at a minimum, be included within the scope of this invention. The worm gear 22 contains non-threaded shoulders 34 of reduced diameter at each end. These shoulders 34 are supported by the sides 36 of the body 20 of the device and serve to support and retain the worm gear 22. Each end of the worm gear 22 also contains a recessed hex socket 24 which provides a means for turning the worm gear 22 from either side of the device.

The lead screw 26 is of a one piece construction but has several functional areas. Smooth, non-threaded head 30 and shoulder 38 on either side of the gear section 40 engage the body of the device and serve to support and retain the lead screw 26. The worm gear 22 couples with the gear section 40 and, as the worm gear 22 is rotated, the lead screw 26 is caused to rotate. The threaded portion 42 of the lead screw 26 interfaces with the carrier 28 and causes the carrier 28 to translate along the axis of the lead screw 26 as the lead screw 26 is turned.

The carrier 28 consists of a flat plate with a perpendicular threaded hole 46 through the plate. The threaded hole 46 engages the threaded portion 42 of the lead screw 26 and translates when the lead screw 26 is turned. The lower surface of the carrier 28 attaches to a fragment of bone which has been trimmed to fit into the area of bony deficit. Attachment of the bone fragment to the carrier 28 is performed by gluing, bonding, cementing, wiring and screwing.

Figure 1C:
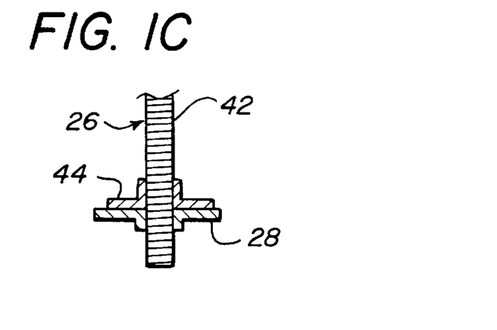
FIG. 1c shows a shield for inhibiting the growth of soft tissue adapted to the lead screw of the present invention.

Referring now to FIG. 1c, a shield 44 adapted to the threaded portion 42 of lead screw 26. The shield 44 can be used to inhibit the growth of soft tissue into the bone growth area.

Figure 2A:
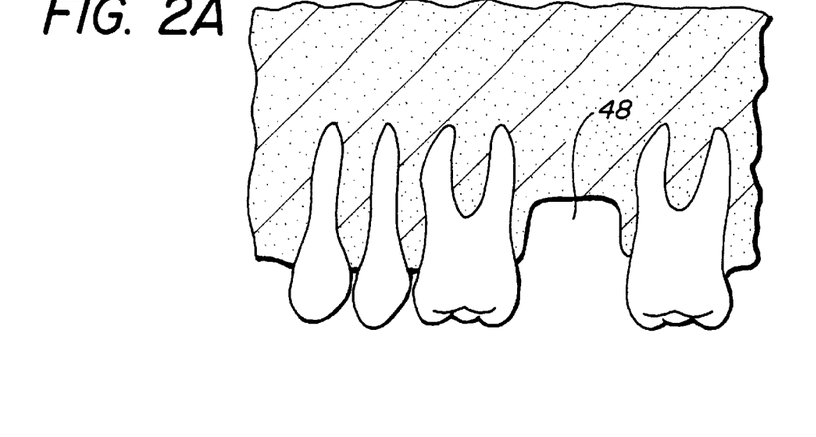
FIG. 2a is a cross-sectional side elevational view of a typical dentoaveolar structure showing an atrophic bone site.
Figure 2B:
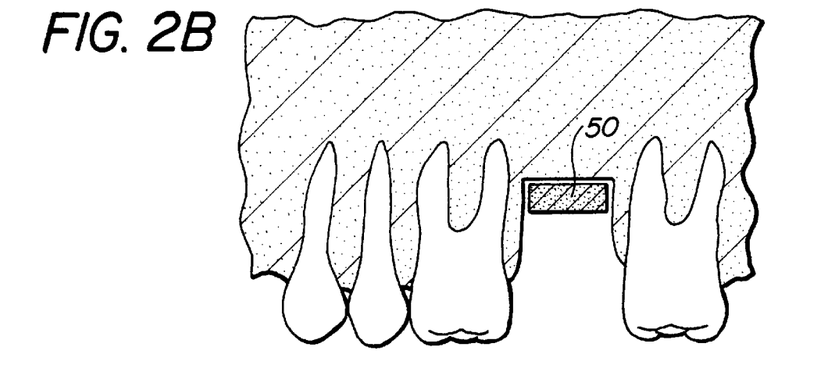
FIG. 2b is the same view of the structure depicted in FIG. 2a also showing a piece of harvested bone in place.
Figure 2C:
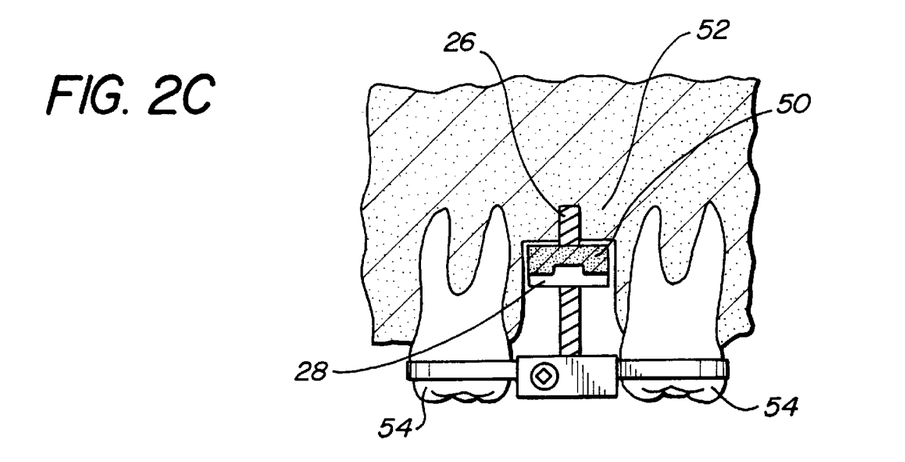
FIG. 2c is the same view of the structure depicted in FIG. 2b illustrating the installation of the device of the present invention.
Figure 2D:
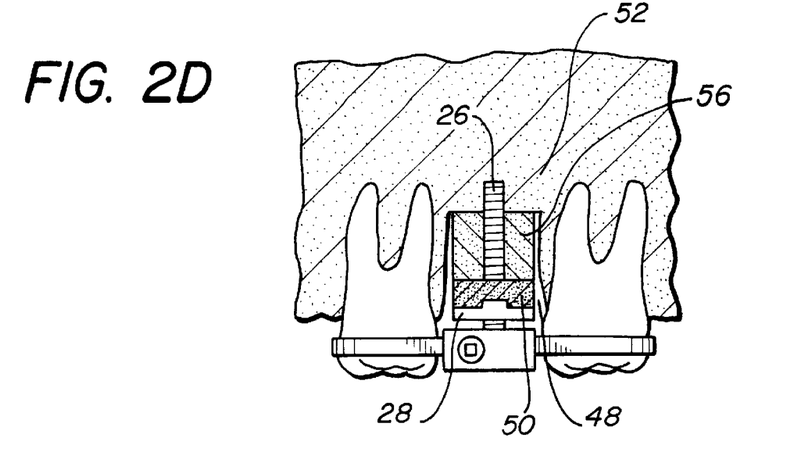
FIG. 2d is the same view of the structure depicted in FIG. 2c illustrating the operation of the device of the invention and newly formed bone in the previously atrophic bone site.
Figure 2E:
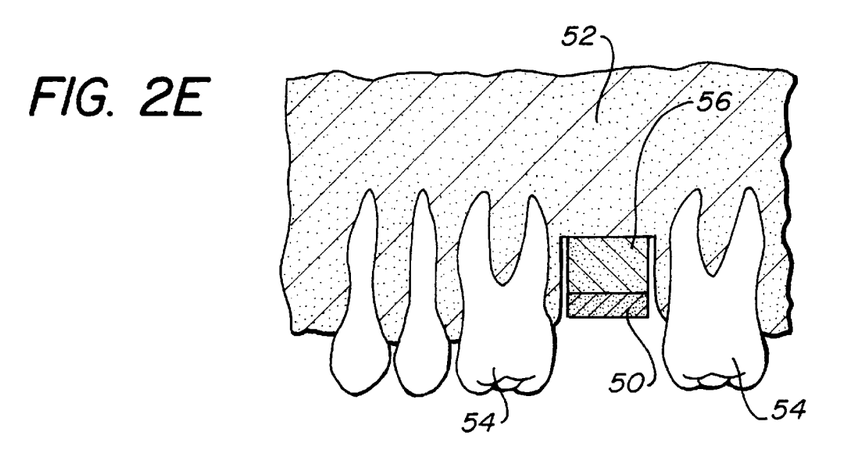
FIG. 2e is the same view of the structure depicted in FIG. 2d illustrating the newly formed bone after removal of the device of the invention.
Figure 2F:
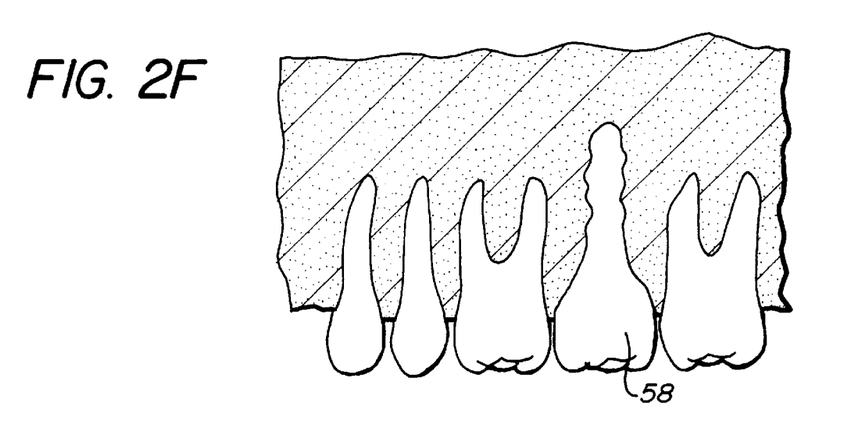
FIG. 2f is the same view of the structure depicted in FIG. 2e illustrating the installation of a dental implant into the newly formed bone in the previously atrophic bone site.

FIGS. 2A through 2F show one of the methods of enhancing the shape, mass, and strength of atrophied alveolar bone in the region of tooth loss. Referring now to FIG. 2A, the atrophic bone site 48 is exposed by reflecting the gum tissue covering it. As can readily be seen in FIG. 2B, a piece of bone 50 is harvested from the area exposed. Referring now to FIG. 2C, the harvested bone 50 is attached to the carrier 28. The carrier 28 with the harvested bone 50 is adapted to the site. The lead screw 26 is threaded through the threaded hole (not shown) of the carrier 28. The lead screw 26 also passes through, but is not threadably engaged with, harvested bone 50 and the underlying bone 52. The carrier 28 and harvested bone 50 are stabilized over the defect and the gum tissue is adapted over the carrier and sutured into place. The body 20 of the device is mounted on the adjacent teeth 54 by cementing or other means for attachment. Referring now to FIG. 2d, after initiation of biological bridging between the harvested bone 50 and the host bone 52, the lead screw 26 is activated to translate the carrier 28 with the harvested bone 50 through the atrophic bone site 48. Activation of the lead screw 26 can be in an intermittent fashion or by continuously gradually rotating the lead screw 26. The newly formed bone 56 grows in the path of motion of the carrier 28 between the harvested bone 50 and the underlying bone 52. The activation of the lead screw 26 is discontinued when the desired bone mass and shape is achieved. This is assessed through clinical evaluations and radiography. As can be readily seen in FIG. 2e, the newly formed bone 56 is allowed to mineralized after which the body (not shown) of the device is dismounted from the adjacent teeth 54. The carrier (not shown) is then exposed by reflecting the gum tissue over it. The carrier (not shown) is detached from the harvested bone 50 and retrieved. The lead screw (not shown) is removed and gum tissue is sutured back to the place. Referring now to FIG. 2f, the site is ready to receive a dental implant 58 or a prosthesis after the gum tissue has healed.

Figure 3A:
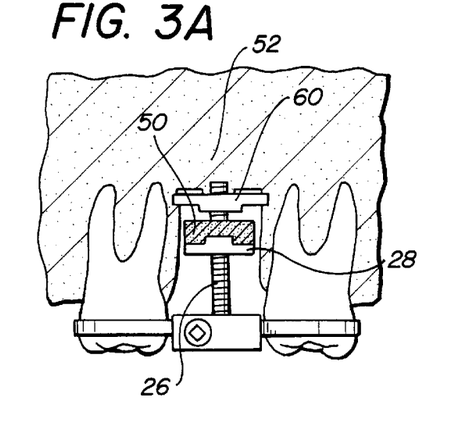
FIG. 3a is a cross-sectional side elevational view of a typical dentoaveolar structure showing another embodiment of the present invention installed into an atrophic bone site.
Figure 3B:
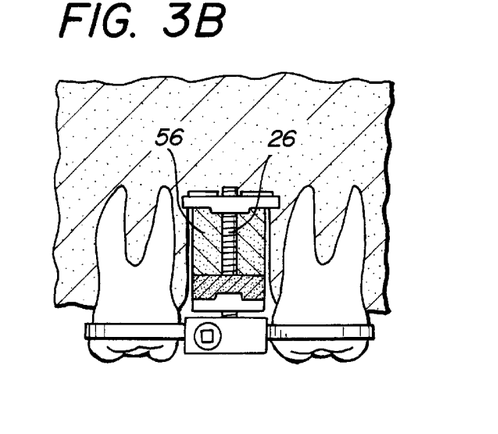
FIG. 3b is the same view depicted in FIG. 3a illustrating the operation of the device of the invention with a infrastructure plate and newly formed bone in the previously atrophic bone site.
Figure 3C:
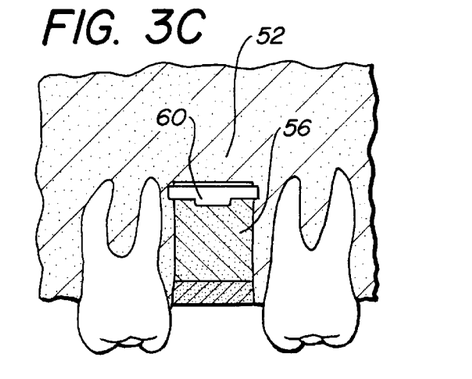
FIG. 3c is the same view depicted in FIG. 3b illustrating the newly formed bone after removal of the device of the invention except for the infrastructure plate.
Figure 3D:
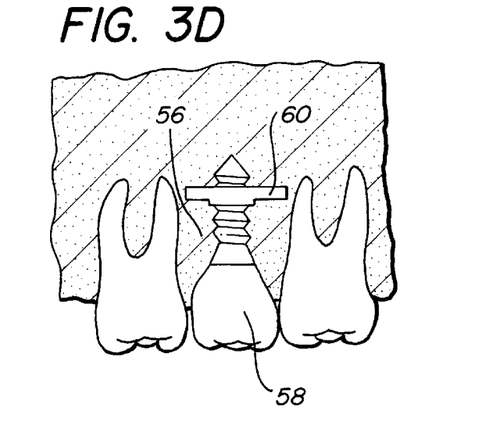
FIG. 3d is the same view depicted in FIG. 3c illustrating the installation of a dental implant into the newly formed bone and infrastructure plate in the previously atrophic bone site.

FIGS. 3a through 3d demonstrate one of the methods of implanting an infrastructure in bone and simultaneously enhancing the shape, mass, and strength of atrophic alveolar bone for increasing the stability of implants against the forces of mastication. The surgical technique is similar to that provided in the preceding embodiment. Referring now to FIG. 3a, an additional infrastructure plate 60 is first stabilized on the underlying bone 52. The infrastructure plate 60 may also be constructed of any bio-compatible material, for example metals such as titanium and its alloys; nickel titanium alloys; zirconia and its alloys; iron and its alloys; and chrome cobalt alloys. The infrastructure plate 60 may be constructed of ceramic materials, such as aluminum oxide, zirconium oxide, titanium oxide, and hydroxylapatite. Fiber reinforced plastics and composites can be used in the construction of the infrastructure plate 60 as well. Bio-absorbable materials, such as poly-L-lactate and polyglycolic acids can be used for the infrastructure plate 60. In addition, these materials may be used in combination with each other. The carrier 28 with the harvested bone 50 is then stabilized over the infrastructure plate 60. The lead screw 26 is threaded into the threaded hole (not shown) of the carrier 28 and passed through the harvested bone 50. The gum tissue (not shown) is sutured back into place. As can be seen in FIG. 3b, the lead screw 26 is activated as described in the previous embodiment to generate newly formed bone 56. As shown in FIG. 3c, once the newly formed bone 56 has achieved the desired level, shape and mass, the body (not shown), lead screw (not shown) and the carrier (not shown) of the device are dismantled leaving the infrastructure plate 60 intact and embedded in the underlying bone 52. As can be readily seen in FIG. 3d, after the newly formed bone 56 has mineralized, the newly formed bone 56 and infrastructure plate 60 is ready to receive a dental implant 58.

Figure 4A:
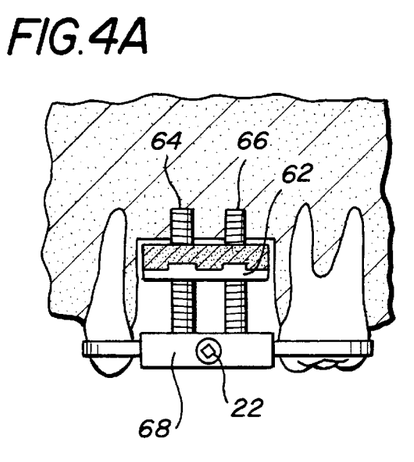
FIG. 4a is a cross-sectional side elevational view of a typical dentoaveolar structure showing another embodiment of the present invention installed into an atrophic bone site.
Figure 4B:
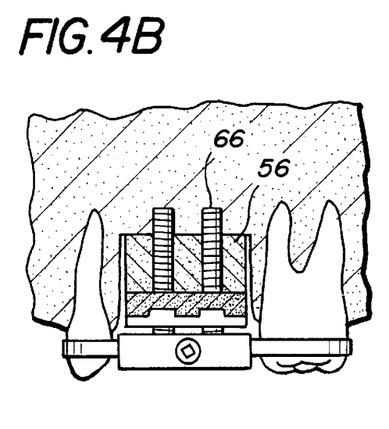
FIG. 4b is the same view depicted in FIG. 4a illustrating the operation of the device of the invention and newly formed bone in the previously atrophic bone site.

FIGS. 4a and 4b show another embodiment that can be used to shape, add mass, and strengthen large areas of alveolar bone. Referring now to FIG. 4a, a device with a single wide bodied carrier 62 with two lead screws 64 and 66 are mounted in a single body 68. The two lead screws 64 and 66 are driven by a single worm gear 22. The process of using this embodiment to generate newly formed bone 56 is the same as described in previous embodiments, and is shown in FIG. 4b. The additional lead screw 66 also provides for increased rotational stability of the device.

Figure 5A:
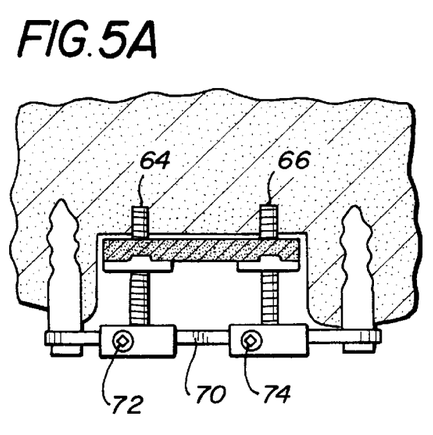
FIG. 5a is a cross-sectional side elevational view of a typical dentoaveolar structure with endosseous dental implants showing another embodiment of the present invention installed into an atrophic bone site.
Figure 5B:
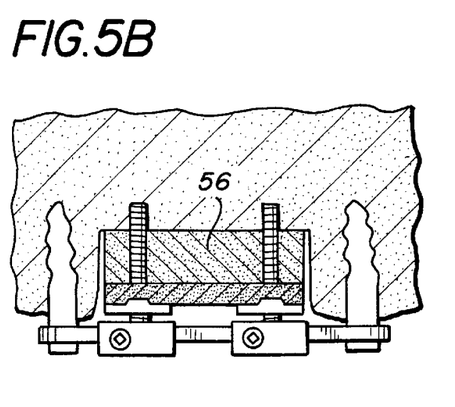
FIG. 5b is the same view depicted in FIG. 5a illustrating the operation of the device of the invention and newly formed bone in the previously atrophic bone site.

Referring now to FIGS. 5a and 5b, another embodiment of the invention is shown that can be used to shape, add mass, and strengthen a large area of atrophied alveolar bone. As seen in FIG. 5a, multiple devices are held on a single frame 70, and their lead screws 64 and 66 are activated by separate worm gears 72 and 74. The devices in this embodiment are shown stabilized against adjacent implants 76, but could as well be stabilized against existing teeth, depending upon the patient. The process of using this embodiment to generate newly formed bone is the same as described in previous embodiments, an is shown in FIG. 5b.

Figure 6A:
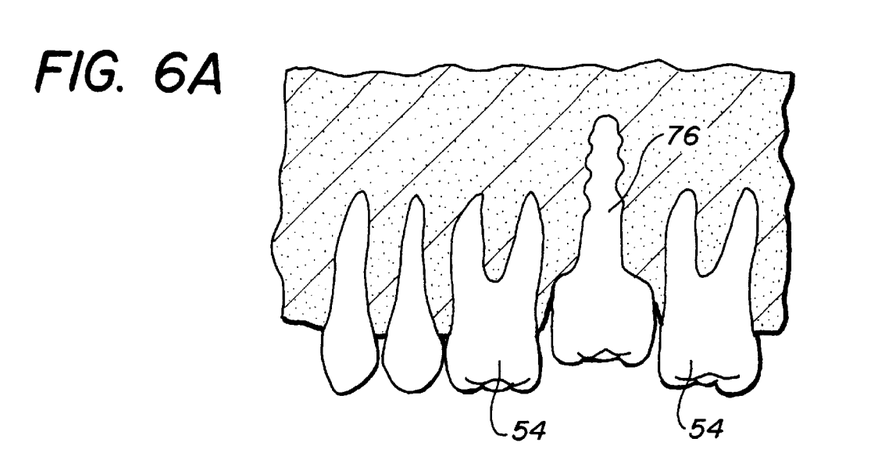
FIG. 6a is a cross-sectional side elevational view of a typical dentoaveolar structure showing an endosseous dental implant submerged with respect to adjacent teeth.
Figure 6B:
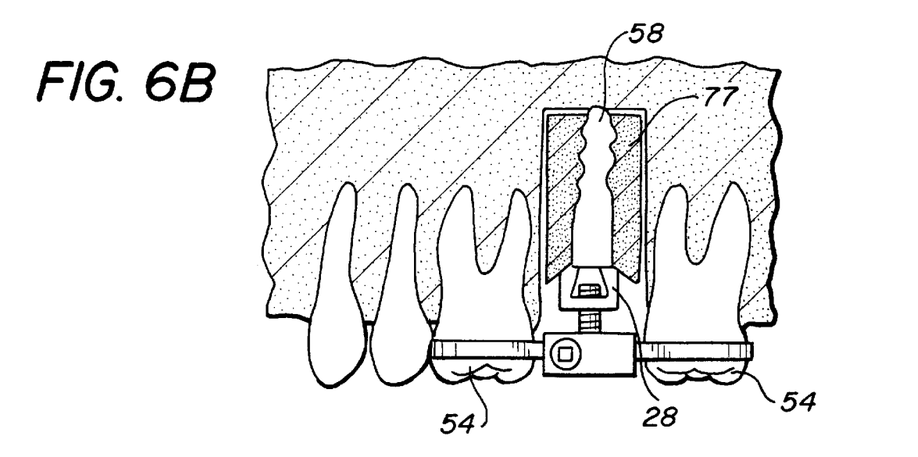
FIG. 6b is the same view depicted in FIG. 6a illustrating the removal of the tooth portion of the implant and installation of one embodiment of the present invention.
Figure 6C:
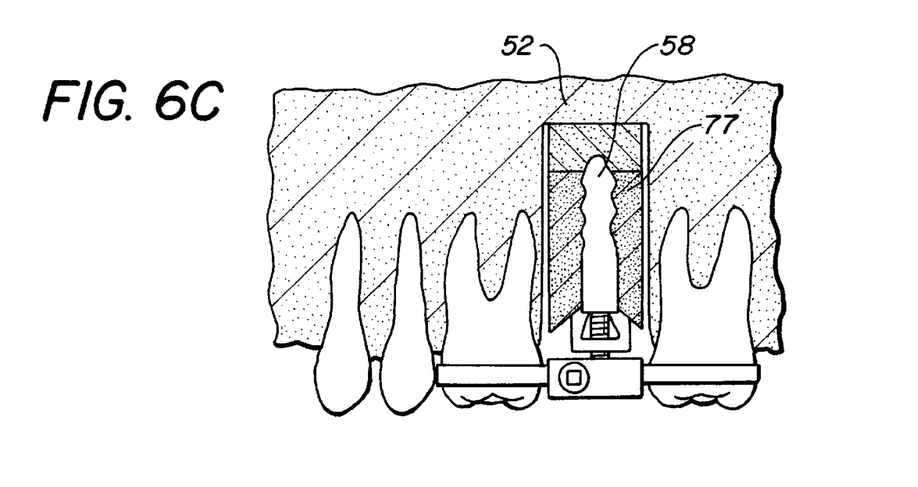
FIG. 6c is the same view depicted in FIG. 6b illustrating the use of the present invention and newly formed bone.
Figure 6D:
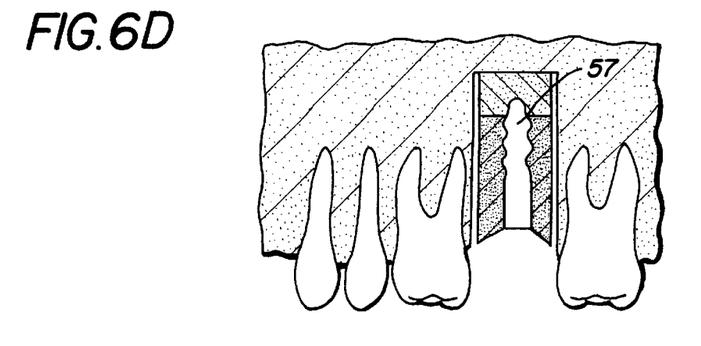
FIG. 6d is the same view depicted in FIG. 6c after the removal of the device of the present invention.
Figure 6E:
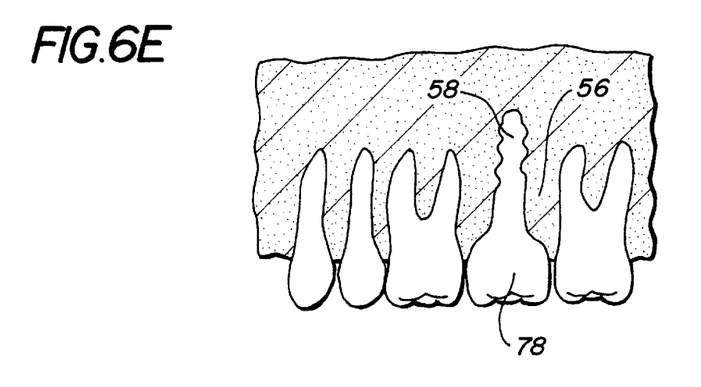
FIG. 6e is the same view depicted in FIG. 6d after mineralization of the newly formed bone and installation of the tooth portion of the dental implant.

FIG. 6a through 6e show an embodiment for elevating a submerged dental endosseous implant to the level of the adjacent teeth. Referring now to FIG. 6a, an implant 76 is shown at a lower level with respect to the adjacent teeth 54. As can be readily seen in FIG. 6b, the tooth portion 78 of the implant has been removed to expose the endosseous implant 58. A partial or complete resection of bone surrounding the implant 58 is made, resulting in a movable bone fragment 77. The carrier 28 is then connected to the top of the implant 58, and the device is attached to adjacent teeth 54. After initiation of biological bridging between the bone fragment 77 and the underlying bone 52, seen in FIG. 6c, the implant 58 and bone fragment 77 are gradually translated into the desired position by the method described in previous embodiments. Referring now to FIG. 6d, after the desired position, bone mass, and bone shape have been achieved, the body (not shown), lead screw (not shown) and the carrier (not shown) of the device are dismantled, leaving the implant 58 in place. The tooth portion 78 of the implant 58 is replaced into the implant 58 after mineralization of the newly formed bone 56 has been completed, as shown in FIG. 6e.

Figure 7A:
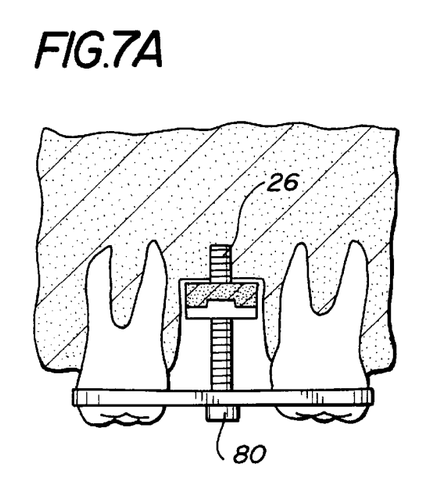
FIG. 7a is a cross-sectional side elevational view of a typical dentoaveolar structure showing another embodiment of the present invention installed into an atrophic bone site.
Figure 7B:
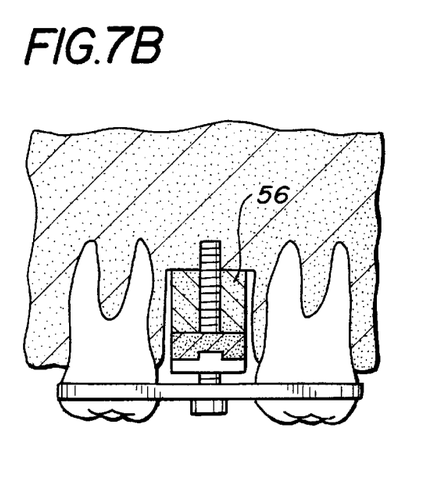
FIG. 7b is the same view depicted in FIG. 7a illustrating the operation of the device of the invention and newly formed bone in the previously atrophic bone site.

In some cases where access between existing teeth or dental implants is limited, a device in which the lead screw is actuated directly is provided. Referring now to FIG. 7a, a device is shown which has no worm gear. The lead screw 26 is activated directly by rotating its head portion 80 in order to translate the carrier 28. The process to generate newly formed bone 56 is the same as described in previous embodiments, and is shown in FIG. 7b.

Figure 8A:
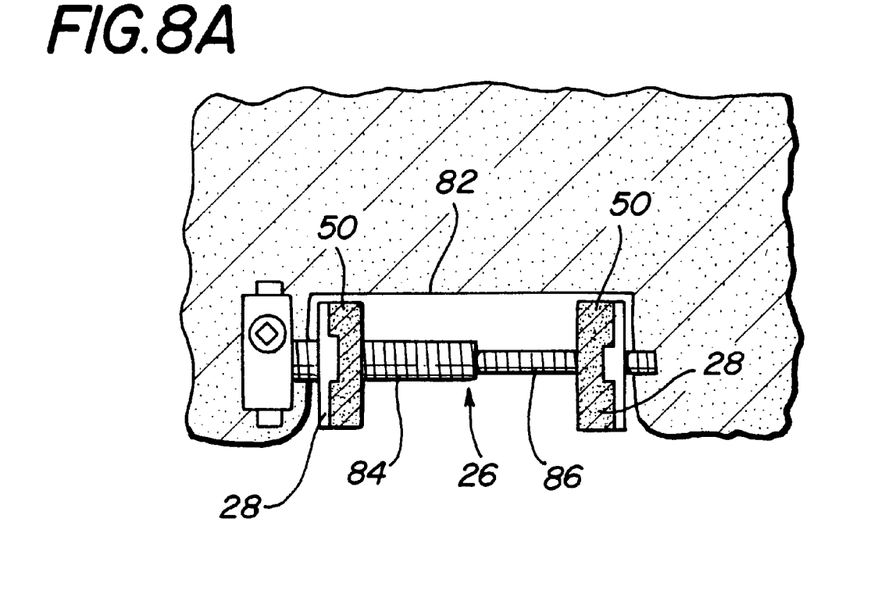
FIG. 8a is a cross-sectional side elevational view of a typical dentoaveolar structure showing yet another embodiment of the present invention installed into a bone site.
Figure 8B:
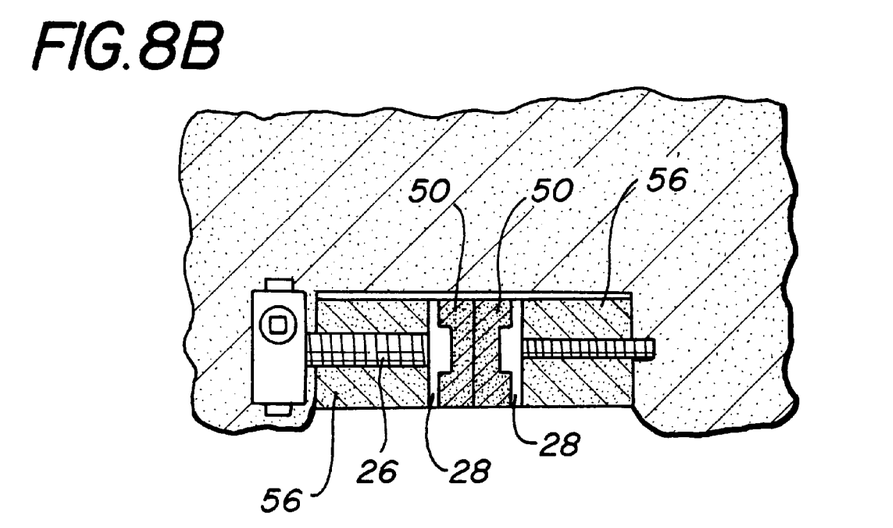
FIG. 8b is the same view depicted in FIG. 8a illustrating the operation of the device of the invention and newly formed bone in the bone site.

Referring now to FIG. 8a, situations exist where rapid closure across large areas of bone deficit is required. The lead screw 26 is constructed to activate two opposing carriers 28 and harvested bone 50 toward each other. The threaded portion of the lead screw 26 is divided into two regions. One region 84 has, for example, a larger diameter with a right-handed thread pitch. The other region 86 has, for example, a smaller diameter and a left-handed thread pitch. One carrier 28 is placed on each portion of the lead screw 26. Looking now to FIG. 8b, as the lead screw 26 is rotated, the carriers 28 and harvested bone 50 translate from the ends of the lead screw 26 toward the center, thereby generating new bone 56.

Figure 9A:
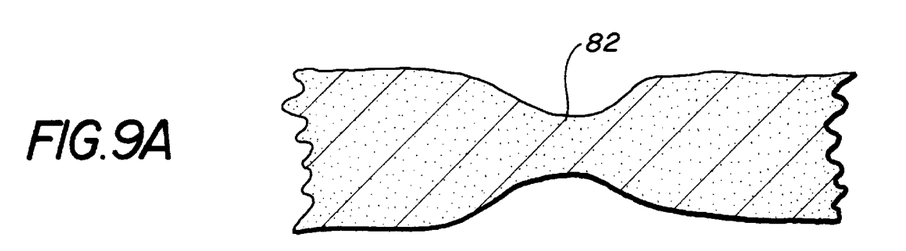
FIG. 9a is a cross-sectional side elevational view of a typical dentoaveolar structure showing an atrophic bone site.
Figure 9B:
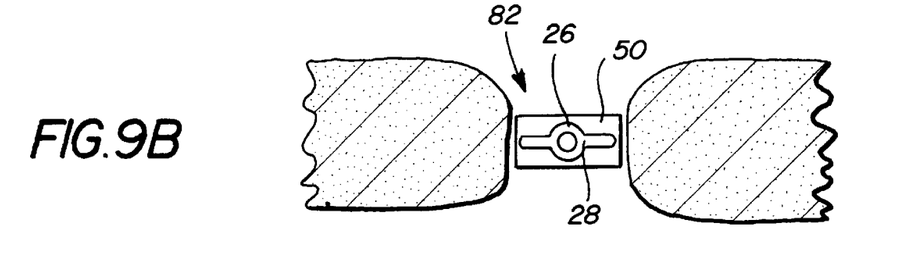
FIG. 9b is the same view of the structure depicted in FIG. 9a also showing a piece of harvested bone and the device of the present invention in place.
Figure 9C:
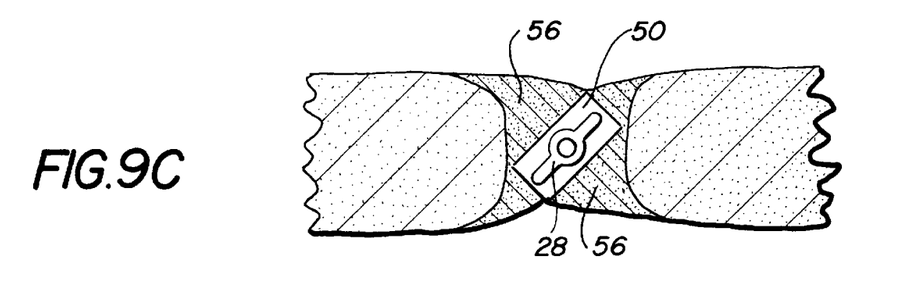
FIG. 9c is the same view of the structure depicted in FIG. 9b illustrating the operation of the device of the present invention and newly formed bone being generated in the atrophic bone site.
Figure 9D:
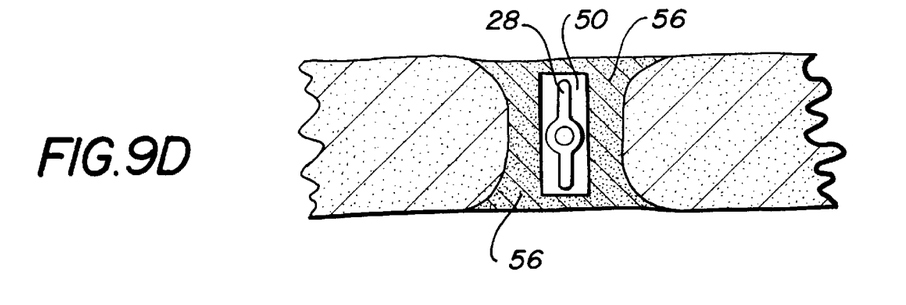
FIG. 9d is the same view of the structure depicted in FIG. 9c illustrating the operation of the device of the invention and newly formed bone filling the previously atrophic bone site.

FIG. 9a shows an area of bony deficit 82. Referring now to FIG. 9b, it is desirable in some situations to utilize rotation of the carrier 28 and harvested bone 50 instead of translation to stimulate and distribute regenerate bone. The carrier 28 is locked to the lead screw 26 so that it rotates with the lead screw 26 instead of translating along the lead screw 26. As can be seen in FIG. 9c, the carrier 28 and any attached bone attractant material 50 is then slowly rotated within or swept through the area of bony deficit 82 to generate new bone. FIG. 9d illustrates complete generation of new bone 56.

Figure 10A:
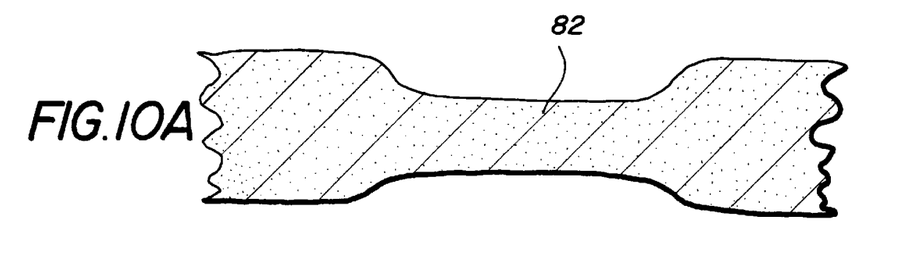
FIG. 10a is a cross-sectional side elevational view of a typical dentoaveolar structure showing an atrophic bone site.
Figure 10B:
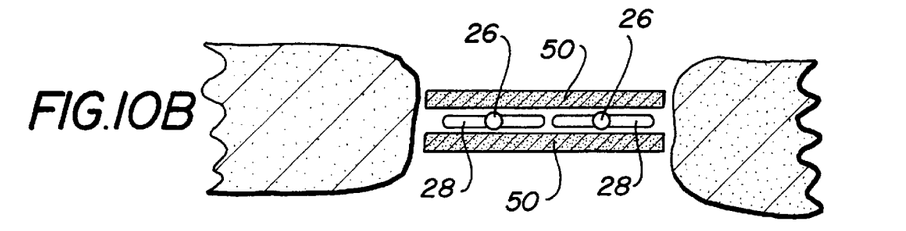
FIG. 10b is the same view of the structure depicted in FIG. 10a also showing two pieces of harvested bone and the device of the present invention in place.
Figure 10C:
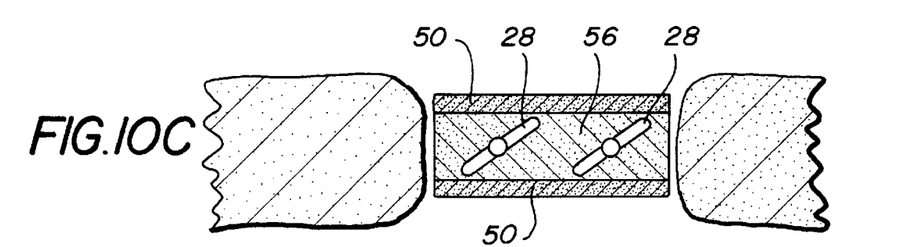
FIG. 10c is the same view of the structure depicted in FIG. 10b illustrating the operation of the device of the present invention and newly formed bone being generated in the atrophic bone site.
Figure 10D:
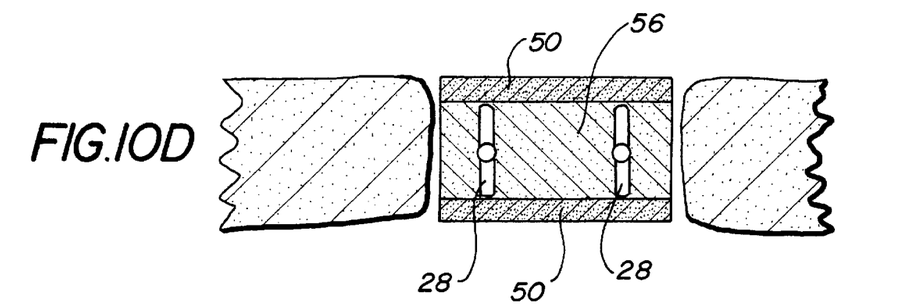
FIG. 10d is the same view of the structure depicted in FIG. 10c illustrating the operation of the device of the invention and newly formed bone filling the previously atrophic bone site.

FIG. 10a also shows an area of bony deficit 82. Referring now to FIGS. 10b through 10d, rotating vertically oriented carriers 28 can also be used for translating pieces of harvested bone 50 or other bone attractant material away from each other thereby generating new bone.

While the preferred embodiments of the present invention have been described so as to enable one skilled in the art to practice the techniques of the present invention, the description of the preferred embodiments is intended to be exemplary and does not limit the scope of the invention in any matter.

What is claimed is:

1. A device for enhancing the shape, mass and strength of bone comprising:
   a bone attractant;
   means for moving said bone gradually over time relative to said bone to generate new bone, said means for moving said bone attractant comprising an electromagnetic actuator.

2. A device for enhancing the shape, mass, and strength of bone comprising:
   a bone attractant:
   a body;
   a lead screw, said lead screw having a gear portion and a threaded portion, said lead screw being at least partially disposed in said body;
   a worm gear, said worm gear engaged with said gear portion of said lead screw for the rotation of said lead screw upon rotation of said worm gear, said worm gear being at least partially disposed in said body;
   a carrier for said bone attractant, said carrier having a threaded hole, said threaded hole being threadably engaged with said threaded portion of said lead screw, said carrier moving along the axis of said lead screw as said lead screw is rotated.

3. The device for enhancing the shape, mass, and strength of bone of claim 2 in which said worm gear comprises a hex socket formed into at least one end of said worm gear.

4. The device for enhancing the shape, mass, and strength of bone of claim 2 further comprising means for attaching said body to dental structures.

5. The device for enhancing the shape, mass, and strength of bone of claim 2 wherein said lead screw is hollow.

6. The device for enhancing the shape, mass, and strength of bone of claim 2 further comprising:
   a shield to inhibit growth of soft tissue, said shield having a hole, said lead screw passing through said hole.

7. A device for enhancing the shape, mass, and strength of bone comprising:
   a body;
   a first lead screw, said first lead screw having a first gear portion and a first threaded portion, said first lead screw being at least partially disposed in said body;
   a second lead screw, said second lead screw having a second gear portion and a second threaded portion, said second lead screw being at least partially disposed in said body;
   a worm gear, said worm gear engaged with said first gear portion of said first lead screw and said second gear portion of said second lead screw for the rotation of said first lead screw and said second lead screw upon rotation of said worm gear, said worm gear being at least partially disposed in said body;
   a carrier, said carrier having a first threaded hole and a second threaded hole, said first threaded hole being threadably engaged with said first threaded portion of said first lead screw, said second threaded hole being threadably engaged with said second threaded portion of said second lead screw, said carrier moving along the axes of said first lead screw and said second lead screw as said first lead screw and said second lead screw are rotated.

8. The device for enhancing the shape, mass, and strength of bone of claim 7 in which said worm gear comprises a hex socket formed into at least one end of said worm gear.

9. A device for enhancing the shape, mass, and strength of bone comprising:
   a frame;
   a first body, said first body attached to said frame;
   a first lead screw, said first lead screw having a first gear portion and a first threaded portion, said first lead screw being at least partially disposed in said first body;
   a first worm gear, said first worm gear engaged with said first gear portion of said first lead screw for the rotation of said first lead screw upon rotation of said first worm gear, said first worm gear being at least partially disposed in said first body;
   a second body, said second body attached to said frame;
   a second lead screw, said second lead screw having a second gear portion and a second threaded portion, said second lead screw being at least partially disposed in said second body;
   a second worm gear, said second worm gear engaged with said second gear portion of said second lead screw for the rotation of said second lead screw upon rotation of said second worm gear, said second worm gear being at least partially disposed in said second body;
   a carrier, said carrier having a first threaded hole and a second threaded hole, said first threaded hole being threadably engaged with said first threaded portion of said first lead screw, said second threaded hole being threadably engaged with said second threaded portion of said second lead screw, said carrier moving along the axes of said first lead screw and said second lead screw as said first lead screw and said second lead screw are rotated.

10. A method for enhancing the shape, mass, and strength of bone, which comprises:
    reflecting soft tissue covering a bone site;
    harvesting a piece of bone from said bone site, thereby revealing underlying bone;
    adapting said harvested bone to said underlying bone;
    waiting for initiation of biological bridging between said harvested bone and said underlying bone;
    moving said harvested bone away from said underlying bone until the desired bone structure is formed.

11. A method for enhancing the shape, mass, and strength of bone, which comprises:
    reflecting soft tissue covering a bone site;
    adapting bone attracting material to said bone site;
    waiting for initiation of biological bridging between said bone attracting material and said bone site;
    moving said bone attracting material away from said bone site until the desired bone structure is formed.

12. The method for enhancing the shape, mass, and strength of bone of claim 11, further comprising the step of adapting a shielding material to the bone site to inhibit the growth of soft tissue.

13. A method for enhancing the shape, mass, and strength of bone, which comprises:
    reflecting soft tissue covering a bone site;
    harvesting a piece of bone from said bone site, thereby revealing underlying bone;
    stabilizing an infrastructure plate to said underlying bone;
    adapting said harvested bone to said infrastructure plate;

waiting for initiation of biological bridging between said harvested bone and said infrastructure plate;

moving said harvested bone away from said infrastructure plate until the desired bone structure is formed.

14. A method for enhancing the shape, mass, and strength of bone, which comprises:

reflecting soft tissue covering a bone site;

stabilizing an infrastructure plate to said bone site;

adapting bone attracting material to said infrastructure plate;

waiting for initiation of biological bridging between said bone attracting material and said infrastructure plate;

moving said bone attracting material away from said infrastructure plate until the desired bone structure is formed.

15. A method for enhancing the shape, mass, and strength of bone, which comprises:

reflecting soft tissue covering alveolar bone adjacent to a dental structure;

cutting bone surrounding said dental structure resulting in said dental structure being movable and encased by a bone fragment and revealing underlying bone;

waiting for initiation of biological bridging between said bone fragment and said underlying bone;

moving said dental structure and said bone fragment away from said underlying bone until the desired bone structure is formed.

16. A device for enhancing the shape, mass, and strength of bone comprising:

a bone attractant;

a frame, said frame having a hole;

a lead screw, said lead screw having a threaded portion, said lead screw passing through said hole in said frame;

a carrier for said bone attractant, said carrier having a threaded hole, said threaded hole being threadably engaged with said threaded portion of said lead screw, said carrier moving along the axis of said lead screw as said lead screw is rotated.

17. A device for enhancing the shape, mass, and strength of bone comprising:

a body;

a lead screw, said first lead screw having a first gear portion, said first lead screw being at least partially disposed in said body, said lead screw having a first threaded portion and a second threaded portion;

a worm gear, said worm gear engaged with said first gear portion of said lead screw for the rotation of said lead screw, said worm gear being at least partially disposed in said body;

a first carrier, said first carrier having a first threaded hole, said first threaded hole being threadably engaged with said first threaded portion of said lead screw, said first carrier moving along the axis of said lead screw toward the center of said lead screw as said lead screw is rotated;

a second carrier, said second carrier having a second threaded hole, said second threaded hole being threadably engaged with said second threaded portion of said lead screw, said second carrier moving along the axis of said lead screw toward the center of said lead screw as said lead screw is rotated.

18. A device for enhancing the shape, mass, and strength of bone comprising:

a bone attractant;

a body;

a lead screw, said lead screw having a gear portion, said lead screw having a first end and a second end, said first end of said lead screw being proximate said gear portion, said lead screw being at least partially disposed in said body;

a worm gear, said worm gear engaged with said gear portion of said lead screw for the rotation of said lead screw upon rotation of said worm gear, said worm gear being at least partially disposed in said body;

a carrier for said bone attractant, said carrier being attached to said second end of said lead screw, said carrier rotating about the axis of said lead screw as said lead screw is rotated for the generation of new bone.

19. A device for enhancing the shape, mass, and strength of bone comprising:

a bone attractant;

a body;

a lead screw, said lead screw having a gear portion, said lead screw having a first end and a second end, said first end of said lead screw being proximate said gear portion, said lead screw being at least partially disposed in said body;

a worm gear, said worm gear engaged with said gear portion of said lead screw for the rotation of said lead screw upon rotation of said worm gear, said worm gear being at least partially disposed in said body;

a carrier for said bone attractant, said carrier being attached to said second end of said lead screw, said carrier rotating about the axis of said lead screw as said lead screw is rotated, said carrier repelling said first bone fragment and said second bone fragment from each other for the generation of new bone.

20. A method for enhancing the shape, mass, and strength of bone, which comprises:

reflecting soft tissue covering a bone site;

harvesting a first piece of bone and a second piece of bone from said bone site, thereby revealing underlying bone;

adapting said first piece of harvested bone to said underlying bone, said underlying bone having a first area and a second area, said first area being opposed said second area;

waiting for initiation of biological bridging between said first piece of harvested bone and said first area of said underlying bone and between said second piece of harvested bone and said second area of underlying bone;

moving said first piece of harvested bone away from said first area of underlying bone and said second piece of harvested bone away from said second area of underlying bone until the desired bone structure is formed.

* * * * *